(12) United States Patent
Boegershausen et al.

(10) Patent No.: US 8,936,636 B2
(45) Date of Patent: Jan. 20, 2015

(54) IMPLANTABLE MEDICAL PROSTHESIS

(75) Inventors: Oliver Boegershausen, Darmstadt (DE); Patrick O'Leary, Babenhausen (DE)

(73) Assignee: Polytech Health & Aesthetics GmbH, Dieburg (DE)

( * ) Notice: Subject to any disclaimer, the term of this patent is extended or adjusted under 35 U.S.C. 154(b) by 0 days.

(21) Appl. No.: 13/572,333

(22) Filed: Aug. 10, 2012

(65) Prior Publication Data

US 2013/0211518 A1 Aug. 15, 2013

(30) Foreign Application Priority Data

Aug. 11, 2011 (EP) ..................................... 11006590

(51) Int. Cl.
*A61F 2/12* (2006.01)
(52) U.S. Cl.
CPC ........... *A61F 2/12* (2013.01); *A61F 2250/0019* (2013.01)
USPC .................................................. 623/8; 623/7
(58) Field of Classification Search
CPC ..................................... A61F 2/12; A61F 2/52
USPC ........................ 623/7, 8, 23.74, 23.64–23.67; 450/50–56
IPC .......................................................... A61F 2/12
See application file for complete search history.

(56) References Cited

U.S. PATENT DOCUMENTS

| 3,671,787 A | 6/1972 | Herron |
| 5,922,023 A | 7/1999 | Mulligan |

FOREIGN PATENT DOCUMENTS

| EP | 0 804 910 A2 | 11/1997 |
| EP | 2 286 761 A1 | 2/2011 |

OTHER PUBLICATIONS

"Diagon\Gel® 4TwoSeries: The Evolutionary Breast Implants," © 2010, Polytech Health & Aesthetics GmbH, Dieburg, Germany, <http://ww.aleamed.be/files/nieuwigheden_lang_00015_pdf.pdf.> [retrieved Dec. 13, 2011], 6-page brochure.
European Search Report dated Dec. 15, 2011, issued in European Patent Application No. EP 11 00 6590, filed Aug. 11, 2011, 6 pages.

*Primary Examiner* — Yashita Sharma
(74) *Attorney, Agent, or Firm* — Christensen O'Connor Johnson Kindness PLLC

(57) ABSTRACT

Implantable medical prosthesis, in particular a breast implant, comprising gel-type filling materials having different rigidities in a specific geometrical arrangement. For example, a breast implant comprises an outer shell and at least one first gel-type filling and at least one second gel-type filling, wherein at least one first gel-type filling has a softer consistency than at least one second gel-type filling, wherein said at least one first gel-type filling extends predominantly along the posterior part of the prosthesis, and wherein said at least one second gel-type filling extends predominantly along the superior portion of the anterior surface of the prosthesis without extending along the entirety of such anterior surface of the prosthesis.

9 Claims, 1 Drawing Sheet

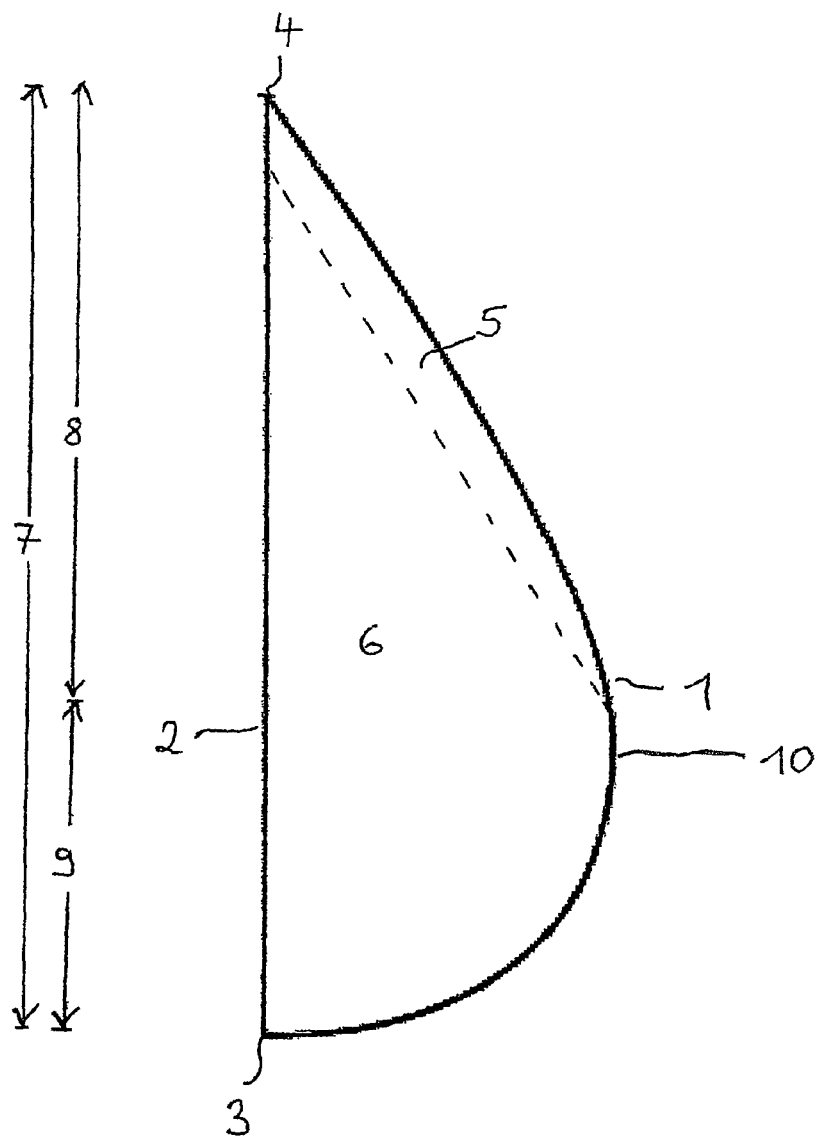

IMPLANTABLE MEDICAL PROSTHESIS

FIELD

The present disclosure relates to an implantable medical prosthesis, and in particular, an implantable internal breast implant.

BACKGROUND

Augmentation or reconstruction of the breast through the use of implantable medical prostheses is commonly used in reconstructive and plastic surgery.

The prostheses used for these procedures have a basic problem associated with the upper pole, namely, insufficient rigidity to maintain the upper pole when in a vertical position. Undesirable alterations of the breast shape are often observed which are commonly referred to as prosthesis wrinkling, knuckling, or scalloping. Usually, these adverse phenomena are observed at the poles of the prosthesis or along the perimeter of the prosthesis shell.

In order to maintain the shape of the upper pole, attempts have been made to use a gel-type filling with a more rigid consistency which, however, leads to a firmer feeling implant, which often appears unnatural and thus is not desirable. On the other hand, a prosthesis with a soft and thus naturally feeling consistency shows a particular risk of the above-mentioned adverse effects.

European Patent Publication No. 0 804 910 discloses an external breast prosthesis of two shell-shaped bodies made of silicone composition of different thickness and each welded into plastic films, the outer body simulating the breast shape and having a hardness matching the soft resilient composition of the natural breast tissue, and the inner body having a softer gel-like consistency which prosthesis is being provided with a permanently tacky adhesive layer which layer comprises first area arranged on the outer prosthesis body and a second area arranged on the inner body thereof.

The prosthesis in accordance with European Patent Publication No. 0 804 910 is not implanted into the body but is attached to the body of the wearer through the mentioned adhesive layers and thus is not a breast implant.

European Patent Publication No. 2 286 761 discloses a form-stable implant comprising an elastomeric shell having anterior and posterior portions, superior and inferior aspects and a perimeter region where the anterior and posterior portions meet, and a plurality of cohesive gel fillers having at least two different degrees of gel cohesiveness. Preferably the gel cohesiveness is greatest at the inferior portion of the implant. According to FIG. 3 of European Patent Publication No. 2 286 761, the gel cohesiveness may be greatest in the upper aspect of the implant. The more cohesive gel is primarily extending along the posterior portion of the implant.

U.S. Pat. No. 3,671,787 discloses a breast prosthesis suitable for implanting into the human breast comprising a container filled with silicone rubber gels of varying stiffness with the stiffest, most viscous gel filling the outer portion of the container and less viscous gels forming further layers with the center portion being filled with the softest material. The outer layers as well as the further layers extend from the anterior part to the posterior part of the container, i.e., they are positioned horizontally.

SUMMARY

Whereas the aforementioned developments have provided some improvements, there still exists a need for further improvement of the properties of respective implantable medical prostheses providing the desired combination of soft natural feeling on one hand and necessary structural rigidity to prevent wrinkling and rippling.

Accordingly, the present disclosure describes improved implantable medical prostheses, in particular for breast augmentation, reconstruction, or correction, showing a reduced tendency for wrinkling while having a natural soft appearance.

The present disclosure relates to an implantable medical prosthesis, in particular a breast implant, comprising an outer shell and at least one first gel-type filling and at least one second gel-type filling, wherein at least one first gel-type filling has a softer consistency than at least one second gel-type filling, and wherein (a) said at least one first gel-type filling extends predominantly along the posterior part of the prosthesis, and (b) said at least one second gel-type filling extends predominantly along the superior portion of the anterior surface of the prosthesis without extending along the entirety of such anterior surface of the prosthesis.

According to a first embodiment of the present disclosure, the at least one first gel-type filling and the at least one second gel-type filling have a common contact area by which they are bonded to each other.

According to a second embodiment, the point of maximum projection of the prosthesis at the anterior side is located in the inferior part of the prosthesis in the range of from 10 to 50% of the entire vertical length of the prosthesis.

According to a further embodiment, the at least one second gel-type filling extends along the anterior surface of the prosthesis from the superior part thereof downwards along about 50 to 90% of the vertical length of the prosthesis.

According to a still further embodiment, at least one of the first and second gel-type filling is bonded to a material forming the outer shell of the prosthesis.

According to another embodiment, the shell volume of the prosthesis is filled by the gel-forming materials to at least 80%, preferably to at least 90%, and particularly preferably to at least 95% of its capacity.

According to still another embodiment, the at least one second gel-type filling having a stiffer consistency than the first gel-type filling extends around at least one edge, even more preferably around the upper and the lower edge of the prosthesis.

The features of the embodiments described above can be combined in any manner, i.e., the prosthesis can realize one or an arbitrary number of the features described above.

DESCRIPTION OF THE DRAWINGS

The foregoing aspects and many of the attendant advantages will become more readily appreciated as the same become better understood by reference to the following detailed description, when taken in conjunction with the accompanying drawings, wherein:

FIG. 1 shows a contour view of an implantable prosthesis in accordance with the present disclosure.

DETAILED DESCRIPTION

The prosthesis comprises an anterior part 1, a posterior part 2, an inferior pole 3, and a superior pole 4. It is apparent to the skilled person that the contour shape of the prosthesis can be subject to a broad range of variations and can be adapted to the individual needs of the patient for whom the prosthesis is intended. As becomes apparent from FIG. 1, within the shell of the prosthesis, two different gel-type fillings are present.

Gel-type filling 5 has a higher rigidity than gel-type filling 6. Gel-type filling 5 extends predominantly along the superior portion of the anterior part of the prosthesis but does not extend along the entirety of the anterior part. The inferior portion of the anterior part of the prosthesis only contains the gel-type filling material 6 having a lower rigidity than gel-type filling 5. Preferably the gel-type filling 5 of higher rigidity extends along the anterior part for the superior portion thereof downwards along about 30% to about 90%, preferably about 45% to about 85% of the vertical length 7 of the prosthesis. In other words, the ratio of part length 8 to the aggregate sum of part length 8 and part length 9 (which corresponds to the vertical length 7) is preferably about 0.30 to about 0.90.

According to another embodiment, the gel-type filling of softer consistency has a rigidity or stiffness similar to the natural breast tissue into which the implant is introduced whereas the more rigid gel-type filling is slightly firmer than the natural breast tissue into which the implant is introduced. This provides a natural appearance of the implant.

According to another embodiment, the gel-type filling with higher rigidity extends along the anterior part of the prosthesis from the superior portion thereof, in particular, from the superior pole towards the inferior portion to the vicinity of the point of maximum projection of the prosthesis which is indicated by reference numeral 10 in FIG. 1. This point of maximum projection usually is preferably located at approximately 10 to 50%, more preferably at approximately 15 to 45%, of the vertical length of the prosthesis, measured from the inferior pole upwards.

The gel-type filling with higher rigidity may extend over the entire width of the anterior surface or it may be constrained to a certain part thereof, preferably approximately symmetrical around a vertical central axis of the prosthesis.

The lateral width of the section with the more rigid gel-type filling in its extension along the anterior part may be constant or it may vary along such extension. The skilled person will select the optimum design depending on the individual body features of the patient for whom the prosthesis is intended and can thus personalize the prosthesis to a high degree.

Generally, in the case of a varying width as outlined above, the width increases with decreasing distance from the anterior part of the prosthesis. However, in principle, any width profile may be chosen depending on the individual patient and thus there are no limitations in this regard.

As for the lateral width, the thickness of the part filled with the gel-type filling of higher rigidity may be chosen in accordance with the individual needs and a constant thickness or a variable thickness, e.g., a tapering profile of thickness may be used. In the case of a tapering thickness profile, the thickness usually increases from the superior portion of the anterior part in towards the lower portion. Preferably, the thickness of the more rigid gel-type filling is reduced on the lateral sides of the prosthesis to give the impression of a softer implant.

The gel-type filling of higher rigidity may comprise a section bound to the posterior surface of the prosthesis or it may not comprise such portion, i.e., the lower rigidity gel-type filling may cover and be bound to the entire posterior surface of the prosthesis. In other words, the gel-type filling of higher rigidity can extend around the upper edge of the prosthesis. In case there is a part of the higher rigidity gel-type filling being in contact with the shell forming the posterior surface of the prosthesis in accordance with the present disclosure (i.e., extending around the upper edge), preferably up to 20%, more preferably up to 10% and most preferably up to 5% of the vertical length 7 of said posterior surface shell of the inventive prosthesis are bound to the rigid gel-type filling, preferably starting from the superior pole 4 of the prosthesis, i.e., the point where anterior and posterior surface meet in the upper part of the prosthesis.

The gel-type filling can also extend around the lower edge of the prosthesis (in the manner described above) or it can extend around both edges (the upper and the lower edge) of the implant. Thus, the skilled person can design the prosthesis according to the individual needs.

The term "gel-type filling," as used herein, generally refers to any material having a degree of elasticity as commonly known for gels, including, but not limited to, gels themselves. The skilled person can choose the suitable material from a broad variety of materials commercially available.

The gel-type filling of lower rigidity constitutes the major part of the entire gel filling of the prosthesis in accordance with the present disclosure, thus providing for a desirable softness in the touch of the prosthesis from the lateral sides.

The outer shell may have a variety of different shapes, e.g., round, conical or anatomical and it may be composed of a variety of different materials altering the surface properties of the shell. Thus, the prosthesis may, e.g., have a smooth or a textured surface or any other surface deemed advantageous in the individual case. As the prosthesis is implanted into the human body and interacts with human tissue while in use, it is important to design the material and the surface of the shell in a manner avoiding adverse interactions or reactions between the tissue of the patient and the material of the shell. Furthermore, the shell material has to prevent leakage of the gel-type filling materials into the human tissue as this may have adverse effects on the patient. Suitable materials have been described in the literature and are known to the skilled person, so that there is no need to give details here. A variety of respective materials, also having necessary regulatory approvals is available from a number of suppliers.

The shell may be elastic and chemically and mechanically resistant. The shell comprises one or more than one layer of a silicone elastomer. If more than one layer is present, the materials of different layers may be the same or different.

Silicone elastomers usually comprise strongly bonded siloxane chains bound to one another in a three-dimensional matrix. Polysiloxane is the chemical term for macromolecules containing alternating oxygen and silicon atoms in the main chain. The length of the chains in polysiloxanes or silicone elastomers may vary from a small number to hundreds or thousands of units. Chain length influences the properties of the final product and thus can be used to tailor a shell material for an individual purpose.

In order to increase mechanical stability, amorphous silica may be added to the siloxane material.

The shell also may comprise a special barrier layer which safely prevents the permeation of low-molecular weight silicone components (which may be present in the gel-type filling material).

Finally, the outer shell surface may be modified to improve the interaction with the human tissue.

As is well known, the human body reacts on foreign bodies with phagocytosis, i.e., it tries to eliminate or to encapsulate the foreign material. However, for breast implants the encapsulation, which is often combined with a dolorous contracture of the capsule, is highly undesirable. In this regard, coating of the silicone-based shell with a material reducing or preventing this interaction has proven to be advantageous under certain circumstances. One suitable material, amongst others, for this purpose is, e.g., a micro-polyurethane foam.

The polyurethane foam may be, e.g., vulcanized on the surface of the materials forming the shell of the prosthesis.

The gel-type filling materials are preferably selected from silicone gels, which are also formed—similar to silicone elastomers—by three-dimensional bonding of polysiloxane chains.

Respective polyurethane foam and gel-type filling material products are commercially available, and there is no need for further details to be given here.

The molecular weight of the polysiloxane (or the chain length) and the degree of bonding or cross-linking of the chains determines the properties of the product and, in particular, the rigidity of the silicone product. Thus by choosing an appropriate chain length and degree of cross-linking, the skilled person can adjust the desired rigidity of the gel-type filling materials over a wide range in accordance with his needs.

Generally, rigidity increases with increasing chain length and increasing degree of cross-linking.

According to one embodiment, the at least one first gel-type filling and the at least one second gel-type filling have a common contact area by which they are bonded to each other. Bonding may be through covalent chemical bonding or weaker coordinate chemical bonding, to give two possible examples.

One of the gel-type filling materials or all gel-type filling materials may be bonded, preferably covalently bonded, to the shell material.

The gel-type filling materials preferably fill at least 80%, more preferably at least 90%, and most preferably at least 95% of the shell volume. Thereby, resistance is provided when the prosthesis is depressed in the anterior to posterior movement.

Implantable medical prostheses in accordance with the present disclosure are most preferably used as breast implants in breast augmentation, reconstruction, or correction. Due to the specific arrangement of gel-type fillings of different rigidity as described before, the prostheses in accordance with the present disclosure provide a particularly good mimicking of the human breast, which is desirable. On one hand, the predominant allocation of material of higher rigidity in the superior portion of the anterior part of the prosthesis provides rigidity to the shell and thus prevents wrinkling of the shell on the anterior surface. By reducing the thickness of the material of high rigidity on the lateral sides in accordance with one embodiment, the implant has a softer touch and provides a desirable softer feeling. On the other hand, allocating the softer gel-type filling in the inferior part of the prosthesis and in the vicinity of the inferior pole allows the push-down of the breast when in a vertical position, thus inducing a slight appearance of ptosis which provides a more natural overall appearance of the prosthesis.

A commercial product available from Inamed Aesthetics under the product name McGhan Style 510 Dual Gel comprises a posterior part of a soft gel and an anterior part of a more rigid gel where the entirety of the anterior part is comprised of the more rigid gel. A series of breast implants under the tradename Diagon/Gel® series is available from Polytech Health & Aesthetics GmbH and which also comprise two different gel fillings. The inferior part is composed of a gel-type filling having higher rigidity whereas the superior part comprises a gel with lower rigidity. The prostheses in accordance with the present disclosure provide a combination of advantageous properties not heretofore achieved to the same extent with other breast implants.

While illustrative embodiments have been illustrated and described, it will be appreciated that various changes can be made therein without departing from the spirit and scope of the claimed subject matter.

The embodiments of the invention in which an exclusive property or privilege is claimed are defined as follows:

1. An implantable medical prosthesis configured as a breast implant, comprising:
   an outer shell;
   at least one first gel filling; and
   at least one second gel filling,
   wherein said at least one first gel filling has a softer consistency than said at least one second gel filling, wherein said at least one first gel filling extends predominantly along a posterior part of the prosthesis, and wherein said at least one second gel filling extends predominantly along a superior portion of an anterior surface of the prosthesis without extending along the entirety of the anterior surface of the prosthesis,
   wherein said at least one first gel filling and said at least one second gel filling have a common contact area by which they are directly bonded to each other,
   wherein said at least one first gel filling or said at least one second gel filling is bonded to a material forming the outer shell of the prosthesis,
   wherein the anterior surface has a point of maximum projection as measured from the posterior part of the prosthesis, and wherein said at least one second gel filling extends along the anterior surface of the prosthesis from the superior portion thereof towards an inferior portion to substantially the point of maximum projection.

2. The implantable medical prosthesis of claim 1, wherein the point of maximum projection of the prosthesis at the anterior side is located in an inferior part of the prosthesis in the range of from 10 to 50% of the entire vertical length of the prosthesis.

3. The implantable medical prosthesis of claim 1, wherein said at least one second gel filling extends along the anterior surface of the prosthesis from a superior portion thereof downwards along about 30 to 90% of the vertical length of the prosthesis.

4. The implantable medical prosthesis of claim 1, wherein the outer shell of the prosthesis is filled by gel-forming materials to at least 80% of its volume capacity.

5. The implantable medical prosthesis of claim 1, wherein the outer shell of the prosthesis is filled by gel-forming materials to at least 90% of its volume capacity.

6. The implantable medical prosthesis of claim 1, wherein the outer shell of the prosthesis is filled by gel-forming materials to at least 95% of its volume capacity.

7. The implantable medical prosthesis of claim 1, wherein the first gel filling constitutes a majority of the entire gel-type filling of the prosthesis.

8. The implantable medical prosthesis of claim 1, wherein said at least one first gel filling and said at least one second gel filling are directly bonded to each other by covalent chemical bonding.

9. The implantable medical prosthesis of claim 1, wherein said at least one first gel filling and said at least one second gel filling are directly bonded to each other by coordinate chemical bonding.

* * * * *

UNITED STATES PATENT AND TRADEMARK OFFICE
CERTIFICATE OF CORRECTION

PATENT NO. : 8,936,636 B2  
APPLICATION NO. : 13/572333  
DATED : January 20, 2015  
INVENTOR(S) : O. Boegershausen et al.

Page 1 of 1

It is certified that error appears in the above-identified patent and that said Letters Patent is hereby corrected as shown below:

In the Claims

| COLUMN | LINE | ERROR |
|---|---|---|
| 6 (Claim 7) | 52 | "entire gel-type" should read --entire gel-- |

Signed and Sealed this
Fourteenth Day of July, 2015

Michelle K. Lee
*Director of the United States Patent and Trademark Office*